United States Patent
Weingartner et al.

(10) Patent No.: US 10,739,420 B2
(45) Date of Patent: Aug. 11, 2020

(54) MOTION-ROBUST TRANSMIT RADIO FREQUENCY FIELD MAPPING IN MAGNETIC RESONANCE IMAGING USING INTERLEAVED BLOCH-SIEGERT SHIFTING

(71) Applicant: Regents of the University of Minnesota, Minneapolis, MN (US)

(72) Inventors: Sebastian Weingartner, Heidelberg (DE); Mehmet Akcakaya, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 132 days.

(21) Appl. No.: 15/697,184

(22) Filed: Sep. 6, 2017

(65) Prior Publication Data

US 2018/0067176 A1 Mar. 8, 2018

Related U.S. Application Data

(60) Provisional application No. 62/384,548, filed on Sep. 7, 2016.

(51) Int. Cl.
| | |
|---|---|
| *G01R 33/24* | (2006.01) |
| *G01R 33/36* | (2006.01) |
| *A61B 5/00* | (2006.01) |
| *G01R 33/48* | (2006.01) |
| *G01R 33/385* | (2006.01) |
| *A61B 5/055* | (2006.01) |
| *G01R 33/565* | (2006.01) |

(52) U.S. Cl.
CPC .......... *G01R 33/246* (2013.01); *A61B 5/0044* (2013.01); *A61B 5/055* (2013.01); *G01R 33/3628* (2013.01); *G01R 33/385* (2013.01); *G01R 33/482* (2013.01); *A61B 5/7285* (2013.01); *G01R 33/56509* (2013.01)

(58) Field of Classification Search
CPC .......... G01R 33/246; G01R 33/3628; G01R 33/385; G01R 33/482; G01R 33/56509; A61B 5/0044; A61B 5/055; A61B 5/7285
See application file for complete search history.

(56) References Cited

U.S. PATENT DOCUMENTS

2014/0117987 A1* 5/2014 Yui .................. G01R 33/28
324/309

OTHER PUBLICATIONS

Clarke WT, et al. Bloch-Siegert B1+-mapping for human cardiac P-MRS at 7 Tesla. Magn Reson Med 2015. doi: 10.1002/mrm.26005.

(Continued)

*Primary Examiner* — Clayton E. LaBalle
*Assistant Examiner* — Michael A Harrison
(74) *Attorney, Agent, or Firm* — Quarles & Brady LLP

(57) ABSTRACT

Systems and methods for mapping the transmit sensitivity of one or more radio frequency ("RF") coils for use in magnetic resonance imaging ("MRI") are described. The transmit RF field ("B1+") for an RF coil, or an array of RF coils, is mapped using a robust, motion-insensitive technique that implements Bloch-Siegert shifts performed with interleaved positive and negative off-resonance shifts. The motion insensitivity of this technique makes it particularly useful for applications where there is significant motion, such as cardiac imaging, in which previous B1+ mapping techniques are not as accurate or effective.

20 Claims, 3 Drawing Sheets

(56) References Cited

OTHER PUBLICATIONS

Cunningham CH, et al. Saturated double-angle method for rapid B1+mapping. Magn Reson Med 2006;55 6):1326-1333.
Deoni SC. High-resolution T1 mapping of the brain at 3T with driven equilibrium single pulse observation of T1 with high-speed incorporation of RF field inhomogeneities (DESPOT1-HIFI). J Magn Reson Imaging 2007;26(4):1106-1111.
Jankiewicz M, et al. Improved encoding pulses for Bloch-Siegert B1(+) mapping. J Magn Reson 2013;226:79-87.
Khalighi MM, et al. Adiabatic RF pulse design for Bloch-Siegert B1+ mapping. Magn Reson Med 2013;70 (3):829-835.
Lau AZ, et al. Integrated Bloch-Siegert B(1) mapping and multislice imaging of hyperpolarized (1)(3)C pyruvate and bicarbonate in the heart. Magn Reson Med 2012;67(1):62-71.
Liu H, et al. Radiofrequency pulse designs for three-dimensional MRI providing uniform tipping in inhomogeneous B(1) Fields. Magn Reson Med 2011;66(5):1254-1266.
Lommen J, et al. Enhancing the quantification of tissue sodium content by MRI: time-efficient sodium B1 mapping at clinical field strengths. NMR Biomed 2016;29(2):129-136.
Pohmann R, et al. A theoretical and experimental comparison of different techniques for B(1) mapping at very high Fields. NMR Biomed 2013;26(3):265-275.
Sacolick Li, et al. B1 mapping by Bloch-Siegert shift. Magn Reson Med 2010;63(5):1315-1322.

Saekho S, et al. Fast-kz three-dimensional tailored radiofrequency pulse for reduced B1 inhomogeneity. Magn Reson Med 2006;55(4):719-724.
Samson RS, et al. A simple correction for B1 field errors in magnetization transfer ratio measurements. Magn Reson Imaging 2006;24(3):255-263.
Saranathan M, et al. Efficient Bloch-Siegert B1 (+) mapping using spiral and echo-planar readouts. Magn Reson Med 2013;70(6):1669-1673.
Schar M, et al. Simultaneous B(0)- and B(1)+-map acquisition for fast localized shim, frequency, and RF power letermination in the heart at 3 T. Magn Reson Med 2010;63(2):419-426.
Schulte RF, et al. Transmit gain calibration for nonproton MR using the Bloch-Siegert shift. NMR Biomed 2011;24 (9):1068-1072.
Sharma A, et al. Highly-accelerated Bloch-Siegert |B1+| mapping using joint autocalibrated parallel image reconstruction. Magn Reson Med 2014;71(4):1470-1477.
Sled JG, et al. Correction for B(1) and B(0) variations in quantitative T(2) measurements using MFI. Magn Reson Med 2000;43(4):589-593.
Sung K, et al. Transmit B1+ field inhomogeneity and T1 estimation errors in breast DCE-MRI at 3 tesla. J Magn Reson Imaging 2013;38(2):454-459.
Sung K, et al. Simultaneous T(1) and B(1) (+) mapping using reference region variable flip angle imaging. Magn Reson Med 2013;70(4):954-961.
Venkatesan R, et al. Accurate determination of spin-density and T1 in the presence of RF-field inhomogeneities and flip-angle miscalibration. Magn Reson Med 1998;40(4):592-602.

* cited by examiner

MOTION-ROBUST TRANSMIT RADIO FREQUENCY FIELD MAPPING IN MAGNETIC RESONANCE IMAGING USING INTERLEAVED BLOCH-SIEGERT SHIFTING

CROSS-REFERENCE TO RELATED APPLICATIONS

This application claims the benefit of U.S. Provisional Patent Application Ser. No. 62/384,548, filed on Sep. 7, 2016, and entitled "System and Method for Motion-Robust Mapping of the Transmit Field in Magnetic Resonance Imaging," which is herein incorporated by reference in its entirety.

STATEMENT REGARDING FEDERALLY SPONSORED RESEARCH

This invention was made with government support under HL111410 and EB015894 awarded by the National Institutes of Health. The government has certain rights in the invention.

BACKGROUND

Quantitative tissue characterization of the myocardium, with its promise for prognostic and diagnostic value in a plethora of cardiomyopathies, has generated considerable research interest and triggered a large number of clinical studies. Available tools for MR-based quantitative tissue characterization in the heart include perfusion imaging, T1-mapping techniques, T2-mapping techniques, and T2*-mapping mapping techniques, and combinations thereof.

Many of these approaches, however, are susceptible to the distribution of the radio frequency ("RF") transmit field ("B1+") and the resulting excitation flip angle. This problem is particularly severe when imaging at high and ultra-high magnetic field strengths, due to the increased heterogeneity of B1+. MR-based quantification accuracy greatly improves when correction for B1+ is included. Therefore, obtaining reliable absolute B1+ magnitude maps (|B1+|) is desirable for achieving accurate quantification in the presence of B1+ heterogeneity.

However, quantification of the transmit B1 fields in the heart remains challenging due to cardiac and respiratory motion, and has received limited attention. Recent studies explored cardiac B1+ mapping using the saturated double angle method ("SDAM"), where |B1+| is derived from the ratio of two images acquired at different flip angles. In SDAM, an additional saturation preparation allows shortening of the repetition time ("TR"), as waiting for full magnetization recovery is no longer required.

Breath-holding is most commonly used in these cardiac B1+ mapping methods for respiratory motion compensation. However, the acquisition of two separate images along with the use of segmented k-space readout schemes causes high sensitivity to motion. Hence, B1+ map quality may be critically impaired by residual motion, as commonly observed in patients despite breath-holding, and remains a major limiting factor for quantitative cardiac imaging.

SUMMARY OF THE DISCLOSURE

The present disclosure addresses the aforementioned drawbacks by providing a system and method for producing a map of a transmit radio frequency ("RF") field generated by an RF coil that forms a part of a magnetic resonance imaging ("MRI") system. Data are acquired from a subject using an MRI system by controlling the MRI system to perform a pulse sequence in which during each repetition time ("TR") period first data and second data are acquired in a temporally interleaved manner. The first data are acquired in a first segment of the pulse sequence by applying a first RF excitation pulse with the RF coil, applying a first off-resonance RF pulse with the RF coil, and acquiring first data after the first off-resonance RF pulse is applied by sampling k-space along a first line. The first off-resonance RF pulse is applied after the first RF excitation pulse and is tuned to a first off-resonance frequency to induce a first Bloch-Siegert shift in the first data. The second data are acquired in a second segment of the pulse sequence by applying a second RF excitation pulse with the RF coil, applying a second off-resonance RF pulse with the RF coil, and acquiring second data after the second off-resonance RF pulse is applied by sampling k-space along a second line. The second off-resonance RF pulse is applied after the second RF excitation pulse and is tuned to a second off-resonance frequency that is different from the first off-resonance frequency to induce a second Bloch-Siegert shift in the second data. The first segment of the pulse sequence and the second segment of the pulse sequence sample different lines of k-space in subsequent TR periods of the pulse sequence, such that the first data and the second data each comprise data acquired by sampling a plurality of different lines in k-space. A transmit RF field (B1+) map is then reconstructed from the first data and the second data.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for mapping the transmit sensitivity of one or more radio frequency ("RF") coils for use in magnetic resonance imaging ("MRI"). The transmit RF field ("B1+") for an RF coil, or an array of RF coils, is mapped using a robust, motion-insensitive technique that implements Bloch-Siegert shifts performed with interleaved positive and negative off-resonance shifts. The motion insensitivity of this technique makes it particularly useful for applications where there is significant motion, such as cardiac imaging, in which previous B1+ mapping techniques are not as accurate or effective.

In MRI, a Bloch-Siegert shift can be generated by applying an off-resonance RF pulse to a nuclear spin, which shifts the resonance frequency of the nuclear spin. In some cases, the off-resonance RF pulse can be designed to be far enough off-resonance that the precession frequency of the nuclear spin is shifted without experiencing excitation from the off-resonance RF pulse. Because the Bloch-Siegert shift is dependent on the strength of the applied B1+ field, these shifts can be used to measure and map the B1+ sensitivity of one or more RF coils.

Figure 1:
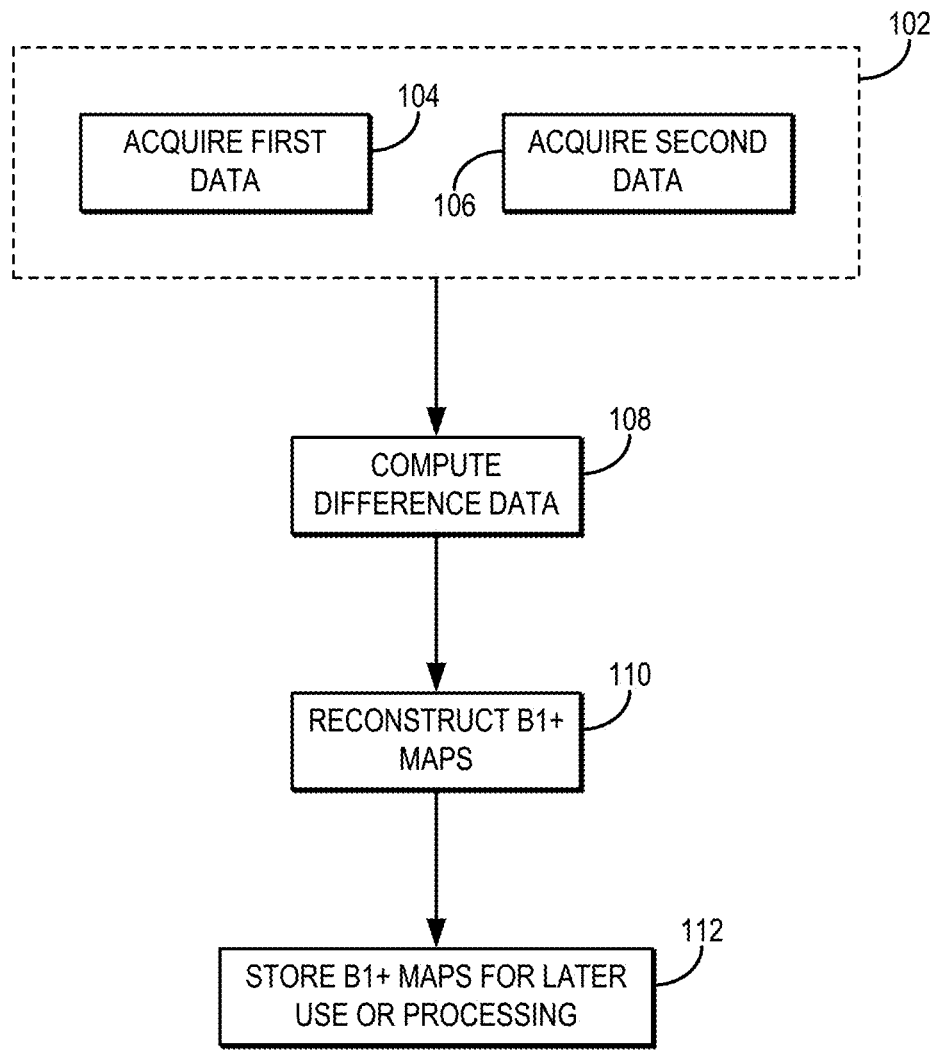
FIG. 1 is a flowchart setting forth the steps of an example method for B1+ mapping using interleaved Bloch-Siegert shifts.

Referring now to FIG. 1, a flowchart is illustrated as setting forth the steps of an example method for generating one or more B1+ maps using Bloch-Siegert shifts. Particularly, positive and negative Bloch-Siegert shifts are induced in an interleaved manner to minimize the impact of motion between images obtained with different Bloch-Siegert shifts. In some embodiments, the Bloch-Siegert shifts are interleaved such that alternating k-space lines in the same acquisition experience different Bloch-Siegert shifts. In some other embodiments, the Bloch-Siegert shifts are interleaved such that the same k-space line is sampled twice in a row: once with a positive shift and once with a negative shift.

The method thus includes acquiring data using an MRI system, as generally indicated at process block 102. The data acquisition includes using a pulse sequence in which data are acquired by sampling k-space using a Cartesian sampling pattern. As one example, the pulse sequence can implement a two-dimensional spoiled gradient ("SPGR") imaging readout. It will be appreciated, however, that data acquisitions with different dimensionality (e.g., one-dimensional, three-dimensional) can also be implemented. In some instances, the data acquisition can be a segmented data acquisition. As one example, k-space can be sampled in a segmented fashion in which a number of lines (e.g., 10) are acquired for each pair of Bloch-Siegert shifts. Even with the use of a segmented acquisition, interleaving the positive and negative off-resonance shifts for each k-space line enables motion robustness in the B1+ mapping procedure by significantly reducing the average delay occurring between the two acquisitions. It will be appreciated that the data acquisition techniques described in the present disclosure can be adapted to includes accelerated data acquisitions, such by using parallel imaging or simultaneous multi-slice imaging, to facilitate multi-slice coverage.

The data acquisition thus generally includes acquiring first data associated with a first Bloch-Siegert shift, as indicated at step 104, and acquiring second data associated with a second Bloch-Siegert shift, as indicated at step 106. The first data are acquired following the application of a first off-resonance RF pulse that is tuned to a first frequency, and the second data are acquired following the application of a second off-resonance RF pulse that is tuned to a second frequency that is different from the first frequency. In general, the first frequency and the second frequency are symmetrically distributed about the resonance frequency of the spins to be excited (e.g., the water resonance peak). Thus, the first frequency and the second frequency can be referred to as a positive frequency, $+\omega_{BS}$, and a negative frequency, $-\omega_{BS}$. In other implementations, however, the first frequency and the second frequency do not need to be symmetrically distributed about the resonance frequency of the spins to be excited, but instead can be generally selected where $\omega_1 \neq \omega_2$.

As one example, the first and second off-resonance RF pulses can be Fermi pulses; however, it will be appreciated that other RF pulse types, such as adiabatic pulses (e.g., adiabatic hyperbolic secant pulses), can also be used. Adiabatic pulses have the added benefit of being able to induce the Bloch-Siegert shift with increased SAR efficiency, which can enable B1+ mapping at ultra-high magnetic field strengths (e.g., 7 T or higher).

In one non-limiting example, the off-resonance RF pulses can be played between a slice rewinder and phase encoding gradient lobes to induce the Bloch-Siegert phase shift, and can have a pulse duration $\tau_{BS}$=8.0 ms, an off-resonance shift $\omega_{BS}$=±4.0 kHz, and a bandwidth containing 99 percent of the pulse energy of 2.1 kHz. In some implementations of this non-limiting example, the total energy of the Fermi pulse can be chosen equivalent to that of a rectangular pulse with a nominal flip angle of 60 degrees.

As mentioned above, the first and second data are acquired in an interleaved manner. In some instances, the first data and the second data can correspond to the same k-space lines; however, in some other instances the first data can include a first set of k-space lines and the second data can include a second set of k-space lines that is different from and interleaved with the first set of k-space lines.

Figure 2:
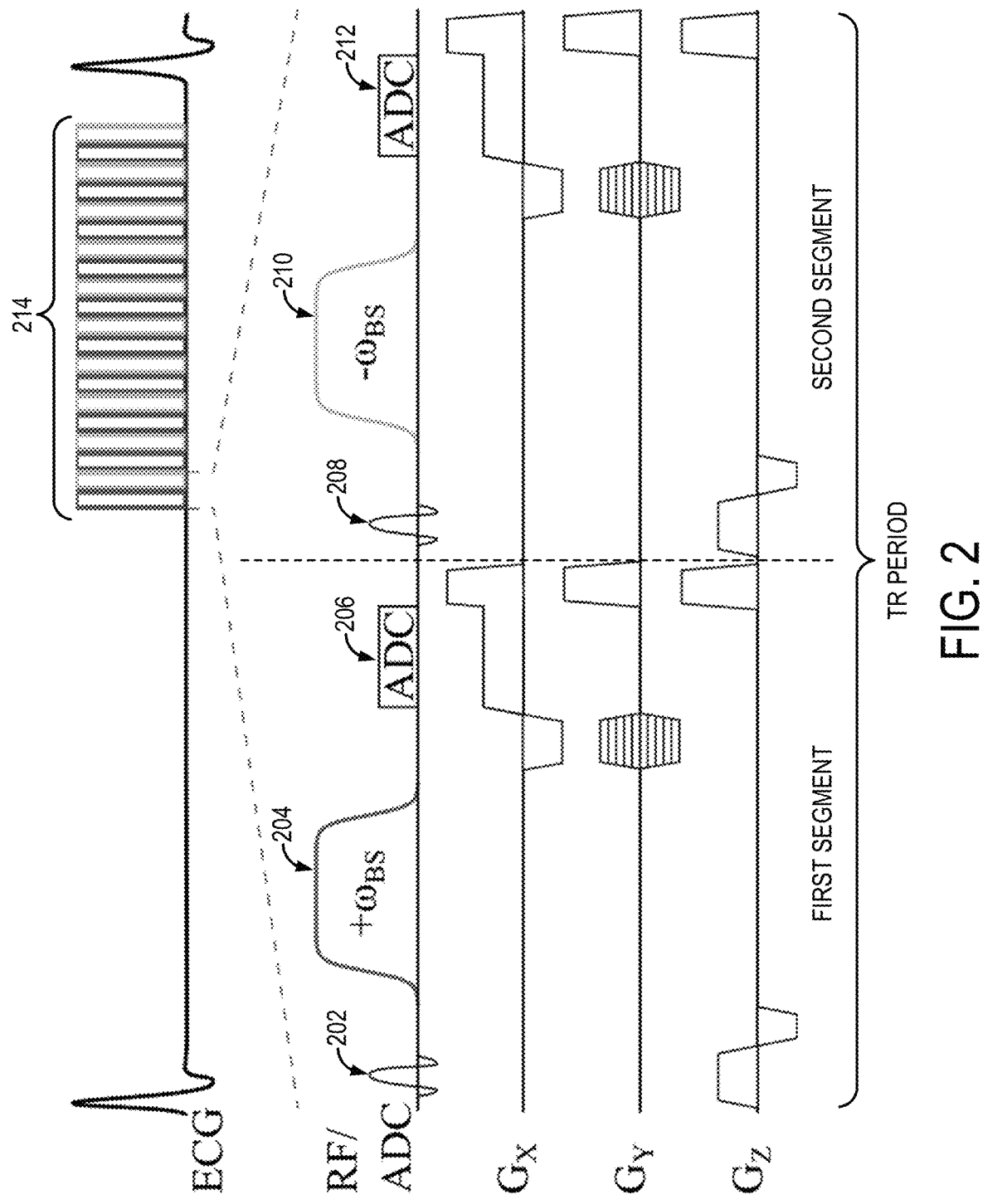
FIG. 2 is a pulse sequence diagram illustrating an example pulse sequence that can be implemented to acquire data for B1+ mapping using interleaved Bloch-Siegert shifts.

As one example, data can be acquired using the pulse sequence shown in FIG. 2. In general, FIG. 2 illustrates on repetition time ("TR") period of the pulse sequence, in which first data are acquired in a first segment of the pulse sequence and second data are acquired in a second segment of the pulse sequence.

In the first segment of the pulse sequence, a first RF excitation pulse 202 is applied to excite spins. A first off-resonance RF pulse 204 is then applied to generate a first Bloch-Siegert shift in the excited spins. As one example, the first off-resonance RF pulse has a frequency corresponding to a positive Bloch-Siegert shift, $+W_{BS}$. Data are then acquired by sampling a k-space line, as indicated at 206. The acquired data are stored in the first set of k-space data.

In the second segment of the pulse sequence, a second RF excitation pulse 208 is then applied to excite the spins again. A second off-resonance RF pulse 210 is then applied to generate a second Bloch-Siegert shift in the excited spins. As one example, the second off-resonance RF pulse has a frequency corresponding to a negative Bloch-Siegert shift, $-\omega_{BS}$. Data are then acquired by sampling the same k-space line and the acquired data, as indicated at 212, and the acquired data are stored in the second set of k-space data. This process is then repeated for different lines in k-space in subsequent TR periods of the pulse sequence, as generally indicated at 214, to form the first and second sets of k-space data. As shown in FIG. 2, the process is repeated for ten different segments of k-space. As also shown in FIG. 2, the pulse sequence can be an ECG-gated sequence, such that data are acquired during the same phase of the cardiac cycle (e.g., during diastolic quiescence).

Referring again to FIG. 1, after the first and second data are acquired, phase difference data are generated by computing the difference between the first and second data, as indicated at step 108. As a result of this subtraction, undesired off-resonance effects due to inhomogeneities in the main magnetic field, $B_0$, and chemical shifts can be eliminated or otherwise reduced. In the event that the first k-space data set and the second k-space data set sample different, but interleaved, lines of k-space, the data can be interpolated or shifted to a similar sampling grid before computing the difference between the first and second data. As one example, generating the phase difference data can include reconstructing first images from the first data, second images from the second data, and computing a difference between the first images and the second images, such as the difference between the phase angles of the first images and the second images (i.e., the phase components of the complex-valued images).

One or more B1+ maps are then generated from the phase difference data, as indicated at step 110. The phase shift encoded in the phase difference data is proportional to the applied B1+ field (i.e., proportional to the square of the transmit RF field magnitude), and thus a B1+ map can be generated based on this relationship. The phase shift can be extracted from k-space data, or from images reconstructed from k-space data. As one example, the B1+ map can be generated based on the following relationship:

$$B_{1,peak} = \sqrt{\frac{\phi_{BS}}{K_{BS}}} \; ; \quad (1)$$

where $B_{1,peak}$ is the peak B1+ of an RF pulse, $\phi_{BS}$ is the phase shift resulting from the Bloch-Siegert shift, and $K_{BS}$ is a constant that describes the phase shift for a given off-resonance RF pulse. As an example, for an 8 millisecond, 4 kHz off-resonance Fermi pulse, $K_{BS}$=74.01 radians/gauss$^2$.

The B1+ maps are then stored for later use or additional processing, as indicated at step 112. For instance, the B1+ maps can be used to adapt or otherwise control the generation of B1+ fields in subsequent imaging scans, or the B1+ maps can be used to generate quantitative parameters maps, such as electrical property maps.

As mentioned above, the B1+ mapping technique described in the present disclosure is particularly useful for mapping the B1+ field in the presence of motion, such as in the presence of cardiac motion, respiratory motion, or both. Thus, while quantitative B1+ mapping in cardiac MRI has been previously challenging because of the presence of cardiac and respiratory motion, the techniques describing in the present disclosure allow for B1+ mapping that is robust against acquisition-specific artifacts, while relying on standard reconstruction techniques commercially available on most MRI systems.

As one example, the B1+ maps can be used to shim the B1+ fields used in subsequent imaging scans. Although 1.5 T magnetic field strengths are still dominant in cardiac MRI, high-field systems are increasingly being used for cardiac applications. Due to dielectric effects that depend on the Larmor frequency, transmit field inhomogeneity is significantly increased in high and ultra-high field applications. Cardiac imaging at ultra-high fields (e.g., 7 T and higher) has recently been facilitated by major advances in hardware engineering, including the availability of multi-channel transmit systems. With these systems, B1+ shimming can be applied to adaptively combine excitation profiles of multi transmit channels, modes, or both, for homogenous excitation profiles. Additionally, tailored RF-excitation pulses have been proposed to compensate for transmit field variabilities. As robust B1+ mapping is a prerequisite for these B1+ shimming and tailored RF-excitation methods, the methods described in the present disclosure can be used to implement these techniques.

Additionally, the robustness of the B1+ mapping techniques described in the present disclosure provide additional advantages to B1+ mapping at higher fields because the B1+ field around the heart at 7T has previously been shown to be dependent on the breathing-state, which can affect the B1+ shimming and calibration unless properly accounted for.

As another example, the B1+ maps can be used for estimating quantitative parameter maps of tissues. Spatial variations in the flip angle have previously been reported to hinder the identification of regional variations induced by pathologies in cardiac MRI. Furthermore, B1+ mapping has been identified as one of the major cofounders in various quantitative imaging applications. The robust mapping of the transmit field provided by the methods described in the present disclosure, however, allows for identification of B1+ induced variations and facilitates accurate quantitative measurements.

As another example, the B1+ maps can be used for mapping electrical properties of a tissue, such as cardiac tissue in the heart. Voxel-wise conductivity and permittivity (i.e., admittivity) mapping can be formulated as an inverse reconstruction problem from B1+ maps using Maxwell's equations, which is described for applications in the brain and the breast by X. Zhang, J. Liu, and B. He, in "Magnetic-resonance-based electrical properties tomography: a review," *IEEE Rev. Biomed. Eng.*, 2014; 7:87-96. Extension of these methods to the heart has been difficult due to the lack of efficient B1+ mapping that is robust to motion and can be acquired in a short scan time.

Using the B1+ mapping techniques described in the present disclosure, accurate B1+ maps can be generated for cardiac imaging applications, even for free-breathing acquisitions. To generate the admittivity maps, complex-valued B1+ maps are generated.

The generation of admittivity properties from B1+ maps is based on solving a differential equation. However, when the reciprocal of admittivity (i.e., impedance per length) is considered and the equations are discretized, a linear system of equations arises. Here, the dependent values and the system matrix are derived from B1+ maps, and the unknown variables correspond to impedance per length, which is a parameter of interest for cardiac imaging. This approach can be implemented with a sparsity-based regularization to improve B1+ map and impedance reconstruction.

Variations in the conductivity and permittivity of tissues depend on changes in intracellular and extracellular volume, ion concentration, and membrane permeability. At frequencies higher than 10 kHz, cell membranes cease to act as capacitive elements, and conductivity increases. At high-field and ultrahigh-field frequencies, membranes expose low impedance to wave propagation, and their conductivity is mostly dictated by their water content. By computing electrical property maps directly from B1+ maps acquired using the methods described in the present disclosure, it is contemplated that a direct visualization of these impedance changes across the heart can be observed.

Figure 3:
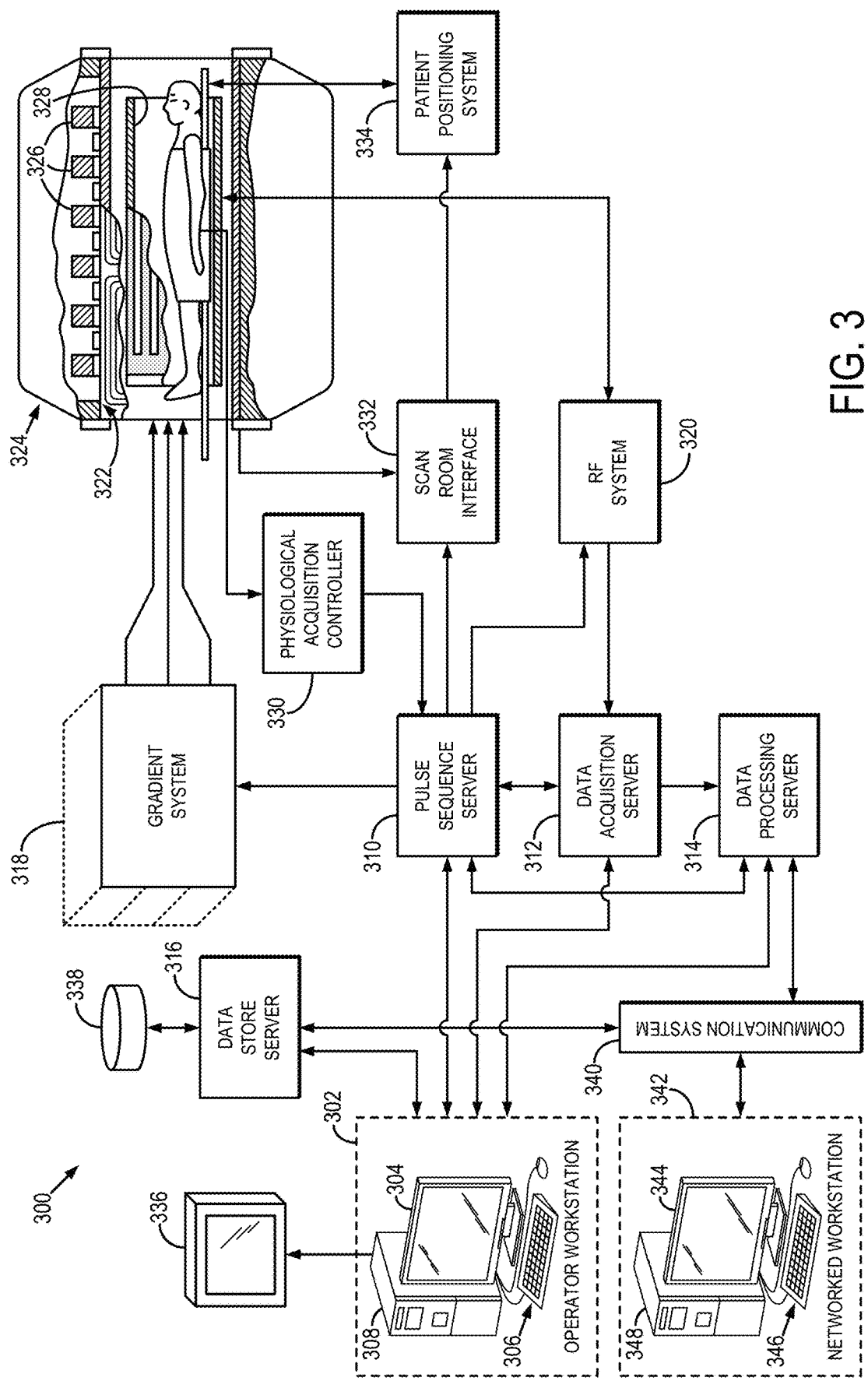
FIG. 3 is a block diagram of an example magnetic resonance imaging ("MRI") system that can implement the methods described in the present disclosure.

Referring particularly now to FIG. 3, an example of an MRI system 300 that can implement the methods described here is illustrated. The MRI system 300 includes an operator workstation 302 that may include a display 304, one or more input devices 306 (e.g., a keyboard, a mouse), and a processor 308. The processor 308 may include a commercially available programmable machine running a commercially available operating system. The operator workstation 302 provides an operator interface that facilitates entering scan parameters into the MRI system 300. The operator workstation 302 may be coupled to different servers, including, for example, a pulse sequence server 310, a data acquisition server 312, a data processing server 314, and a data store server 316. The operator workstation 302 and the servers 310, 312, 314, and 316 may be connected via a communication system 340, which may include wired or wireless network connections.

The pulse sequence server 310 functions in response to instructions provided by the operator workstation 302 to operate a gradient system 318 and a radiofrequency ("RF") system 320. Gradient waveforms for performing a prescribed scan are produced and applied to the gradient system 318, which then excites gradient coils in an assembly 322 to produce the magnetic field gradients $G_x$, $G_y$, and $G_z$ that are used for spatially encoding magnetic resonance signals. The gradient coil assembly 322 forms part of a magnet assembly 324 that includes a polarizing magnet 326 and a whole-body RF coil 328.

RF waveforms are applied by the RF system 320 to the RF coil 328, or a separate local coil to perform the prescribed magnetic resonance pulse sequence. Responsive magnetic resonance signals detected by the RF coil 328, or a separate local coil, are received by the RF system 320. The responsive magnetic resonance signals may be amplified, demodulated, filtered, and digitized under direction of commands produced by the pulse sequence server 310. The RF system 320 includes an RF transmitter for producing a wide variety of RF pulses used in MRI pulse sequences. The RF transmitter is responsive to the prescribed scan and direction from the pulse sequence server 310 to produce RF pulses of the desired frequency, phase, and pulse amplitude waveform. The generated RF pulses may be applied to the whole-body RF coil 328 or to one or more local coils or coil arrays.

The RF system 320 also includes one or more RF receiver channels. An RF receiver channel includes an RF preamplifier that amplifies the magnetic resonance signal received by the coil 328 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2} \quad (2);$$

and the phase of the received magnetic resonance signal may also be determined according to the following relationship:

$$\varphi = \tan^{-1}\left(\frac{Q}{I}\right). \quad (3)$$

The pulse sequence server 310 may receive patient data from a physiological acquisition controller 330. By way of example, the physiological acquisition controller 330 may receive signals from a number of different sensors connected to the patient, including electrocardiograph ("ECG") signals from electrodes, or respiratory signals from a respiratory bellows or other respiratory monitoring devices. These signals may be used by the pulse sequence server 310 to synchronize, or "gate," the performance of the scan with the subject's heart beat or respiration.

The pulse sequence server 310 may also connect to a scan room interface circuit 332 that receives signals from various sensors associated with the condition of the patient and the magnet system. Through the scan room interface circuit 332, a patient positioning system 334 can receive commands to move the patient to desired positions during the scan.

The digitized magnetic resonance signal samples produced by the RF system 320 are received by the data acquisition server 312. The data acquisition server 312 operates in response to instructions downloaded from the operator workstation 302 to receive the real-time magnetic resonance data and provide buffer storage, so that data is not lost by data overrun. In some scans, the data acquisition server 312 passes the acquired magnetic resonance data to the data processor server 314. In scans that require information derived from acquired magnetic resonance data to control the further performance of the scan, the data acquisition server 312 may be programmed to produce such information and convey it to the pulse sequence server 310. For example, during pre-scans, magnetic resonance data may be acquired and used to calibrate the pulse sequence performed by the pulse sequence server 310. As another example, navigator signals may be acquired and used to adjust the operating parameters of the RF system 320 or the gradient system 318, or to control the view order in which k-space is sampled. In still another example, the data acquisition server 312 may also process magnetic resonance signals used to detect the arrival of a contrast agent in a magnetic resonance angiography ("MRA") scan. For example, the data acquisition server 312 may acquire magnetic resonance data and processes it in real-time to produce information that is used to control the scan.

The data processing server 314 receives magnetic resonance data from the data acquisition server 312 and processes the magnetic resonance data in accordance with instructions provided by the operator workstation 302. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 314 are conveyed back to the operator workstation 302 for storage. Real-time images may be stored in a data base memory cache, from which they may be output to operator display 302 or a display 336. Batch mode images or selected real time images may be stored in a host database on disc storage 338. When such images have been reconstructed and transferred to storage, the data processing server 314 may notify the data store server 316 on the operator workstation 302. The operator workstation 302 may be used by an operator to archive the images, produce films, or send the images via a network to other facilities.

The MRI system 300 may also include one or more networked workstations 342. For example, a networked workstation 342 may include a display 344, one or more input devices 346 (e.g., a keyboard, a mouse), and a processor 348. The networked workstation 342 may be located within the same facility as the operator workstation 302, or in a different facility, such as a different healthcare institution or clinic.

The networked workstation 342 may gain remote access to the data processing server 314 or data store server 316 via the communication system 340. Accordingly, multiple networked workstations 342 may have access to the data processing server 314 and the data store server 316. In this manner, magnetic resonance data, reconstructed images, or other data may be exchanged between the data processing server 314 or the data store server 316 and the networked workstations 342, such that the data or images may be remotely processed by a networked workstation 342.

The present disclosure has described one or more preferred embodiments, and it should be appreciated that many equivalents, alternatives, variations, and modifications, aside from those expressly stated, are possible and within the scope of the invention.

The invention claimed is:

1. A method for producing a map of a transmit radio frequency (RF) field generated by an RF coil that forms a part of a magnetic resonance imaging (MRI) system, the steps of the method comprising:
acquiring data from a subject using an MRI system by controlling the MRI system to perform a pulse sequence in which during each repetition time (TR) period first data and second data are acquired in a temporally interleaved manner by,
acquiring the first data in a first segment of the pulse sequence by:
applying a first RF excitation pulse with an RF coil;
applying a first off-resonance RF pulse with the RF coil after applying the first RF excitation pulse, wherein the first off-resonance RF pulse is tuned to a first off-resonance frequency to induce a first Bloch-Siegert shift in the first data;
acquiring the first data after the first off-resonance RF pulse is applied by sampling k-space along a first line;
acquiring the second data in a second segment of the pulse sequence by:
applying a second RF excitation pulse with the RF coil;
applying a second off-resonance RF pulse with the RF coil after applying the second RF excitation pulse, wherein the second off-resonance RF pulse is tuned to a second off-resonance frequency that is different from the first off-resonance frequency to induce a second Bloch-Siegert shift in the second data;
acquiring the second data after the second off-resonance RF pulse is applied by sampling k-space along a second line;
wherein the first segment of the pulse sequence and the second segment of the pulse sequence sample different lines of k-space in subsequent TR periods of the pulse sequence such that the first data and the second data each comprise data acquired by sampling a plurality of different lines in k-space; and
reconstructing a transmit RF field (B1+) map from the first data and the second data.

2. The method as recited in claim 1, wherein the first line and the second line sample a same line of k-space in each TR period.

3. The method as recited in claim 1, wherein the first line and the second line sample different adjacent lines of k-space in each TR period.

4. The method as recited in claim 1, wherein reconstructing the B1+ map comprises generating phase difference data by computing a difference between the first data and the second data, and reconstructing the B1+ map from the phase difference data.

5. The method as recited in claim 1, wherein the first off-resonance frequency and the second off-resonance frequency are symmetrically distributed about a resonance frequency to which the first RF excitation pulse and the second RF excitation pulse are tuned.

6. The method as recited in claim 1, wherein the first data and the second data are acquired using a two-dimensional data acquisition.

7. The method as recited in claim 1, wherein the first off-resonance RF pulse and the second off-resonance RF pulse are Fermi pulses.

8. The method as recited in claim 1, wherein the first off-resonance RF pulse and the second off-resonance RF pulse are adiabatic RF pulses.

9. The method as recited in claim 1, wherein the pulse sequence is an electrocardiograph (ECG) triggered pulse sequence such that subsequent repetitions of the TR period occur during a same phase of a cardiac cycle.

10. The method as recited in claim 1, wherein the RF coil comprises an array of RF coil elements, and the pulse sequence is repeated to acquire first data and second data for each RF coil element in the array of RF coil elements, and wherein a B1+ map is reconstructed for each RF coil element in the array of RF coil elements from the respective first data and second data.

11. The method as recited in claim 1, further comprising calculating B1+ shim parameters for the RF coil using the reconstructed B1+ map.

12. The method as recited in claim 1, further comprising calculating a quantitative parameter of a tissue in the subject using the B1+ map.

13. The method as recited in claim 12, wherein the quantitative parameter is an electrical property of the tissue.

14. The method as recited in claim 13, wherein the electrical property is an admittivity of the tissue.

15. The method as recited in claim 14, wherein the tissue is cardiac tissue.

16. A magnetic resonance imaging (MRI) system, comprising:
a magnet system configured to generate a polarizing magnetic field about at least a portion of a subject arranged in the MRI system;
a plurality of gradient coils configured to apply at least one gradient field to the polarizing magnetic field;
a radio frequency (RF) system including an RF coil to apply an RF field to the subject and to acquire magnetic data therefrom;
a computer system programmed to:
acquire data from a subject by controlling the plurality of gradient coils and the RF system to perform a pulse sequence in which during each repetition time (TR) period first data and second data are acquired in a temporally interleaved manner by,
acquiring the first data in a first segment of the pulse sequence by:
applying a first RF excitation pulse with an RF coil;
applying a first off-resonance RF pulse with the RF coil after applying the first RF excitation pulse, wherein the first off-resonance RF pulse is tuned to a first off-resonance frequency to induce a first Bloch-Siegert shift in the first data;
acquiring the first data after the first off-resonance RF pulse is applied by sampling k-space along a first line;
acquiring the second data in a second segment of the pulse sequence by:
applying a second RF excitation pulse with the RF coil;
applying a second off-resonance RF pulse with the RF coil after applying the second RF excitation pulse, wherein the second off-resonance RF pulse is tuned to a second off-resonance frequency that is different from the first off-resonance frequency to induce a second Bloch-Siegert shift in the second data;

acquiring the second data after the second off-resonance RF pulse is applied by sampling k-space along a second line;

wherein the first segment of the pulse sequence and the second segment of the pulse sequence sample different lines of k-space in subsequent TR periods of the pulse sequence such that the first data and the second data each comprise data acquired by sampling a plurality of different lines in k-space; and reconstruct a transmit RF field (B1+) map from the first data and the second data.

17. The MRI system as recited in claim 16, wherein the first line and the second line sample a same line of k-space in each TR period.

18. The MRI system as recited in claim 16, wherein the first line and the second line sample different adjacent lines of k-space in each TR period.

19. The MRI system as recited in claim 16, wherein the computer system is programmed to reconstruct the B1+ map by generating phase difference data by computing a difference between the first data and the second data, and reconstructing the B1+ map from the phase difference data.

20. The MRI system as recited in claim 16, wherein the first off-resonance frequency and the second off-resonance frequency are symmetrically distributed about a resonance frequency to which the first RF excitation pulse and the second RF excitation pulse are tuned.

* * * * *